United States Patent
Koseoglu et al.

(10) Patent No.: US 10,807,947 B2
(45) Date of Patent: Oct. 20, 2020

(54) CONTROLLED CATALYTIC OXIDATION OF MEROX PROCESS BY-PRODUCTS IN INTEGRATED REFINERY PROCESS

(71) Applicant: Saudi Arabian Oil Company, Dhahran (SA)

(72) Inventors: Omer Refa Koseoglu, Dhahran (SA); Robert Peter Hodgkins, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 16/210,514

(22) Filed: Dec. 5, 2018

(65) Prior Publication Data

US 2020/0181073 A1 Jun. 11, 2020

(51) Int. Cl.
| | | |
|---|---|---|
| *C07C 315/02* | (2006.01) | |
| *B01D 53/50* | (2006.01) | |
| *B01J 23/30* | (2006.01) | |
| *C10G 27/12* | (2006.01) | |

(52) U.S. Cl.
CPC ............ *C07C 315/02* (2013.01); *B01D 53/50* (2013.01); *B01J 23/30* (2013.01); *C10G 27/12* (2013.01)

(58) Field of Classification Search
CPC ...... C07C 315/02; C10G 27/12; C10G 19/02; C10G 2300/202; C10G 27/06; C10G 53/12; C10G 53/14; B01D 53/50; B01D 11/0492; B01J 23/30
See application file for complete search history.

(56) References Cited

U.S. PATENT DOCUMENTS

| | | | |
|---|---|---|---|
| 4,052,445 A | 10/1977 | Schreyer et al. | |
| 4,729,835 A * | 3/1988 | McNeillie | C02F 1/722 210/759 |
| 4,992,578 A * | 2/1991 | Husain | C07C 381/04 560/307 |
| 2017/0158972 A1* | 6/2017 | Koseoglu | C10G 21/16 |

FOREIGN PATENT DOCUMENTS

| | | | |
|---|---|---|---|
| EP | 0005073 | * | 10/1979 |
| WO | WO2017072190 | * | 5/2017 |

OTHER PUBLICATIONS

Engel et al. (Remove mercaptans from hydrocarbon condensates and NGL streams, pp. 1-6, published Feb. 2016) (Year: 2016).*
Anisimov et al. (Year: 1994).*
Trost et al. (New Synthetic Reactions. A Chemoselective Approach to Cleavage a to a Carbonyl Group via ß-Keto Sulfides. Preparation of 1,2-Diketones, JACS, 99:13 pp. 4405-4412, Published Jun. 1977) (Year: 1977).*
Anisimov, AV, Oxidation of Disulfides by Hydrogen-Peroxide Under Interphase Catalysis Conditions, Petroleum Chemistry, vol. 34, No. 5, 1994, 1 page.

\* cited by examiner

*Primary Examiner* — Yevgeny Valenrod
*Assistant Examiner* — Blaine G Doletski
(74) *Attorney, Agent, or Firm* — Abelman, Frayne & Schwab

(57) ABSTRACT

An integrated controlled catalytic oxidation process converts low value disulfide oil (DSO) compounds produced as a by-product of a generalized mercaptan oxidation (MEROX) process into oxidized DSO (ODSO) compounds including sulfoxides, sulfones, sulfonates and sulfinates that are completely or partially water soluble and which have utility, e.g., as lubricity additives in diesel fuel and as a solvent in aromatic solvent separation processes.

21 Claims, 6 Drawing Sheets

CONTROLLED CATALYTIC OXIDATION OF MEROX PROCESS BY-PRODUCTS IN INTEGRATED REFINERY PROCESS

FIELD OF THE INVENTION

This disclosure is directed to an integrated refinery process for the treatment of the disulfide oil (DSO) compounds that are produced as a by-product of the mercaptan oxidation (MEROX) process.

BACKGROUND OF THE INVENTION

The mercaptan oxidation (MEROX) process that has long been employed for the removal of the generally foul smelling mercaptans found in many hydrocarbon streams was introduced to the refining industry over fifty years ago. Because of regulatory requirements to reduce the sulfur content of fuels for environmental reasons, refineries have been, and continue to be faced with the disposal of large volumes of sulfur-containing by-products.

Disulfide oil (DSO) compounds are produced as a by-product of the MEROX process in which the mercaptans are removed from any of a variety of petroleum streams including liquefied petroleum gas, naphtha, and other hydrocarbon fractions. It is commonly referred to as a 'sweetening process' because it removes the sour or foul smelling mercaptans present in crude petroleum. The term "DSO" is used for convenience in this description and in the claims, and will be understood to include the mixture of disulfide oils produced as by-products of the MEROX process.

The designation "MEROX" originates from the function of the process itself, i.e., the conversion of mercaptans by oxidation. The MEROX process in all of its applications is based on the ability of an organometallic catalyst in a basic environment, such as a caustic, to accelerate the oxidation of mercaptans to disulfides at near ambient temperatures and pressures. The overall reaction can be expressed as follows:

$$RSH + \tfrac{1}{4}O_2 \rightarrow \tfrac{1}{2}RSSR + \tfrac{1}{2}H_2O \qquad (1)$$

where R is a hydrocarbon chain that may be straight, branched, or cyclic, and the chains can be saturated or unsaturated. In most petroleum fractions, there will be a mixture of mercaptans so that the R can have 1, 2, 3 up to 10 or more carbon atoms in the chain. This variable chain length is indicated by R and R' in the reaction. The reaction is then written:

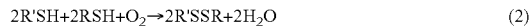

$$2R'SH + 2RSH + O_2 \rightarrow 2R'SSR + 2H_2O \qquad (2)$$

This reaction occurs spontaneously, but at a very slow rate, whenever any sour mercaptan-bearing distillate is exposed to atmospheric oxygen. In addition, the catalyzed reaction (1) requires the presence of an alkali caustic solution, such as sodium hydroxide. The mercaptan oxidation proceeds at an economically practical rate at moderate refinery downstream temperatures.

The MEROX process can be conducted on both liquid streams and on combined gas and liquid streams. In the case of liquid streams, the mercaptans are converted directly to disulfides which remain in the product so that there is no reduction in total sulfur content of the effluent stream. Because the vapor pressures of disulfides are relatively low compared to those of mercaptans, their presence is much less objectionable from the standpoint of odor; however, they are not environmentally acceptable and their disposal can be difficult. The MEROX process typically utilizes a fixed bed reactor system for liquid streams and is normally employed with charge stocks having end points above 135°-150° C. Mercaptans are converted to disulfides in the fixed bed reactor system over a catalyst, for example, an activated charcoal impregnated with the MEROX reagent, and wetted with caustic solution. Air is injected into the hydrocarbon feedstream ahead of the reactor and in passing through the catalyst-impregnated bed, the mercaptans in the feed are oxidized to disulfides. The disulfides are substantially insoluble in the caustic and remain in the hydrocarbon phase. Post treatment is required to remove undesirable by-products resulting from known side reactions such as the neutralization of $H_2S$, the oxidation of phenolic compounds, entrained caustic, and others.

In the case of mixed gas and liquid streams, extraction is applied to both phases of the hydrocarbon streams. The degree of completeness of the mercaptan extraction depends upon the solubility of the mercaptans in the alkaline solution, which is a function of the molecular weight of the individual mercaptans, the extent of the branching of the mercaptan molecules, the concentration of the caustic soda and the temperature of the system. Thereafter, the resulting DSO compounds are separated and the caustic solution is regenerated by oxidation with air in the presence of the catalyst and reused.

Referring to the attached drawings, FIG. 1 is a simplified schematic of a generalized conventional version of the prior art MEROX process of liquid-liquid extraction for removing sulfur compounds in an embodiment in which a combined propane and butane hydrocarbon stream (1) containing mercaptans is treated and which includes the steps of:

introducing the hydrocarbon stream (1) into an extraction vessel (10) with a homogeneous cobalt-based catalyst in the presence of caustic (2);

passing the hydrocarbon stream in counter-current flow through the extraction section of the extraction (10) vessel in which the extraction section includes one or more liquid-liquid contacting extraction decks or trays (not shown) for the catalyzed reaction with the circulating caustic solution to convert the mercaptans to water soluble alkali metal alkane thiolate compounds;

withdrawing a hydrocarbon product stream (3) that is free or substantially free of mercaptans from the extraction vessel (10);

recovering a combined spent caustic and alkali metal alkane thiolate stream (4) from the extraction vessel (10);

subjecting the spent caustic to catalyzed wet air oxidation in a reactor (20) into which is introduced catalyst (5) and air (6) to provide the regenerated spent caustic (8) and convert the alkali metal alkane thiolate compounds to disulfide oils; and recovering a by-product stream (7) of disulfide oil (DSO) compounds and a minor proportion of sulfides.

The effluents of the wet air oxidation step in the MEROX process preferably comprise a minor proportion of sulfides and a major proportion of disulfide oils. As is known to those of skill in the art, the composition of this effluent stream depends on the effectiveness of the MEROX process, and sulfides are assumed to be carried-over material. A variety of catalysts have been developed for the commercial practice of the process. The efficiency of the MEROX process is also a function of the amount of $H_2S$ present in the stream. It is a common refinery practice to install a prewashing step for $H_2S$ removal.

The disulfide oil compounds produced in the MEROX process can contain various disulfides. For example, a MEROX unit designed for the recovery of propane and butane yields a disulfide oil mixture with the composition set forth in Table 1:

TABLE 1

| Disulfide Oil | W % | BP | MW | Sulfur, W % |
|---|---|---|---|---|
| Dimethyldisulfide | 15.7 | 110 | 94 | 68.1 |
| Diethyldisulfide | 33.4 | 152 | 122 | 52.5 |
| Methylethyldisulfide | 49.3 | 121 | 108 | 59.3 |
| Total | 98.4 | 127.69 | 109 | 57.5 |

Table 1 indicates the composition of the disulfide oil that is derived from semi-quantitative GC-MS data. No standards were measured against the components; however, the data in Table 1 is accurate in representing relative quantities. Quantitative total sulfur content was determined by energy dispersive x-ray fluorescence spectroscopy which indicated 63 wt % of sulfur, and this value will be used in later calculations. The GC-MS results provide evidence for trace quantities of tri-sulfide species; however, the majority of the disulfide oil stream comprises the three components identified in Table 1.

The by-product disulfide oils produced by the MEROX unit can be processed and/or disposed of in various other refinery units operations. For example, the DSO can be added to the fuel oil pool at the expense of a resulting higher sulfur content of the pool. The DSO can be processed in a hydrotreating/hydrocracking unit at the expense of higher hydrogen consumption. The disulfide oil also has an unpleasant foul or sour smell, which is somewhat less prevalent because of its relatively lower vapor pressure at ambient temperature; however, there are problems in the handling of this oil.

Thus, there is a clear and long-standing need to provide an efficient and economical process for the treatment of the large volumes of DSO by-products to effect and modify its properties in order to facilitate and simplify its environmentally acceptable disposal, and/or to permit the utilization of the modified products within the refinery, and thereby enhance the value of this class of by-products to the refiner.

It will be understood that references in this disclosure to the generalized MEROX process also include equivalent processes for the oxidation of mercaptans in hydrocarbon streams that result in the production of DSO by-products. The term "MEROX" as used herein will be understood to be a general reference to include the proprietary process and as generalized mercaptan oxidation.

SUMMARY OF THE INVENTION

The present disclosure is directed to an integrated process for use in conjunction with the MEROX process or other mercaptan oxidation process, to treat the liquid disulfide oils (DSO) produced as by-products of the MEROX process in a controlled catalyzed oxidation reaction to convert the DSO compounds to sulfoxides, sulfones, sulfonates and sulfonates that are entirely or partially water soluble. The solubility of these oxidation products facilitates their subsequent handling, treatment and their economically beneficial use directly or in downstream processes to produce higher value product streams.

An important aspect of the integrated process of the present disclosure is the ability to control the degree or extent of the oxidation to produce compounds that are water soluble or water insoluble. The process can advantageously be operated continuously either with the feed from the MEROX process, or its equivalent, or with disulfide oils from a storage or surge tank as required to accommodate refinery production schedules.

The disulfide oil stream from the MEROX process is oxidized in the presence of a catalyst to produce a mixture of water insoluble sulfur compounds, e.g., sulfoxides, disulfoxides and sulfones, or completely water soluble sulfoxide sulfonates/sulfinates, sulfone sulfonates/sulfinates, disulfones and sulfone sulfoxides by controlling the degree or extent of the oxidation. The totally water soluble components, which can be tailored to constitute 100% of the catalyzed reaction products, can be disposed conveniently and economically in a refinery without significant environmental impact.

The following examples describe the short chain disulfide oil by-products produced in the treatment of feeds for the purpose of recovering propane and butane from which the sulfur compounds had been removed. The oxidation products from the caustic regeneration unit were identified as dimethyldisulfide, methylethyldisulfide and diethyldisulfide. It is to be understood, however, that the catalytic oxidation process of this disclosure can be practiced on both short chain compounds comprising methyl and ethyl groups, and on longer chain DSO by-products, including both straight and branched chains, up to C20.

The disulfide oils having the general formula RSSR produced in the MEROX process can be oxidized without or with one or more catalysts to produce an oxidized disulfide oil (ODSO) for use as solvents in accordance with the present disclosure. If a catalyst is used in the oxidation of the disulfide oils (RSSR) to produce the oxidized disulfide oil (ODSO), it can be a heterogeneous or homogeneous oxidation catalyst. The oxidation catalyst can be selected from one or more heterogeneous or homogeneous catalysts comprising metals from IUPAC Groups 4-12 of the Periodic Table, including Ti, V, Mn, Co, Fe, Cr, Cu, Zn, W and Mo. In certain embodiments, suitable homogeneous catalysts include molybdenumacetylacetonate, bis(acetylacetonate) dioxomolybdenum, molybdenum naphthanate, sodium tungstate, molybdenum hexacarbonyl, tungsten hexacarbonyl, sodium tungstate and vanadium pentoxide. In certain embodiments, suitable heterogeneous catalysts include Ti, V, Mn, Co, Fe, Cr W, Mo, and combinations thereof deposited on a support such as alumina, silica-alumina, silica, titania, natural zeolites, synthetic zeolites, and combinations comprising one or more of the above supports. A presently preferred catalyst is sodium tungstate, $Na_2WO_4 \cdot 2H_2O$. A suitable catalyst compound is commercially available, e.g., from Sigma-Alrich Co., LLC of St. Louis, Mo. In certain embodiments, the catalyst has a pore volume in the range of from 0.2 to 1.2 cc/g, preferably from 0.6 to 0.9 cc/g, a total surface area in the range of from 20 to 800 $m^2/g$, preferably from 100 to 400 $m^2/g$, and an average pore diameter in the range of from 2 to 1000 nm, preferably from 5 to 50 nm.

For oxidation, Lewis acidity and the oxidation potential of the catalyst are important parameters. If the catalyst has a high oxidation potential then it will decompose the oil. Although not wishing to be bound to a specific theory, the reaction mechanism appears to include the Lewis acid metal forming a complex with the reactant disulfides and peroxides, which complex then becomes an active species.

The integrated refinery process of the present disclosure treats the DSO compounds recovered from a generalized MEROX process by the controlled catalytic oxidation of the disulfide oils including water soluble sulfoxide sulfonates/sulfinates, sulfone sulfonates/sulfinates, disulfones and sulfone sulfoxides and the recovery of the oxidized disulfide oil (ODSO) and a waste water stream. The ODSO stream can contain compounds with up to 6 oxygen atoms.

The oxidant can be a liquid peroxide selected from the group consisting of alkyl hydroperoxides, aryl hydroperoxides, dialkyl peroxides, diaryl peroxides, peresters and hydrogen peroxide. The perester can have the general formula $R_1C=O-O-O-R_2$, wherein $R_1$ and $R_2$ are the same or different alkyl or aryl groups.

The oxidant can be a gas, including air, oxygen, ozone and oxides of nitrogen.

The oxidant can be a liquid oxidant including one or more organic hydroperoxides, organic peroxides, and a combination of one or more organic hydroperoxides and organic peroxides, and one or more gas phase oxidants selected from the group consisting of one or more of air, oxygen, oxides of nitrogen and ozone.

The catalyst is preferably a homogeneous water soluble compound that is a transition metal containing an active species selected from the group consisting of Mo (VI), W (VI), V (V), Ti (IV), and their combinations.

In the practice of the integrated process of this disclosure for the controlled catalytic oxidation of the by-product disulfide oil compounds from the wet air oxidation of the alkali metal alkane thiolates, the molar ratio of oxidant to mono-sulfur in the disulfide compounds present can be in the range of from about 1:1 to 50:1, preferably from 1:1 to 25:1, and most preferably from 1:1 to 5:1. The molar ratio of the catalyst present in the DSO oxidation step (catalyst/DSO molar ratio) can be in the range from about 0.0005 to 0.02, or from 0.0015 to 0.01. The catalyst present in the DSO oxidation step can be in the range of from about 0.15 weight % to about 5.7 weight %, or from 0.3 wt. % to 3 wt. % based on the mass flow rate of the sulfides/DSO mixture.

As will be described below, the ODSO compounds have utility in various refinery operations where their relatively high sulfur content does not have a significant adverse environmental impact because they are blended in relatively low concentrations with other products or recovered for recycling and continuous use in a closed system. These new ODSO compounds provide the refiner with added value from a problematic, low value by-product of the MEROX process.

BRIEF DESCRIPTION OF THE DRAWINGS

The invention will be described in more detail below and in conjunction with the attached drawings in which.

DETAILED DESCRIPTION OF THE INVENTION

Figure 1:
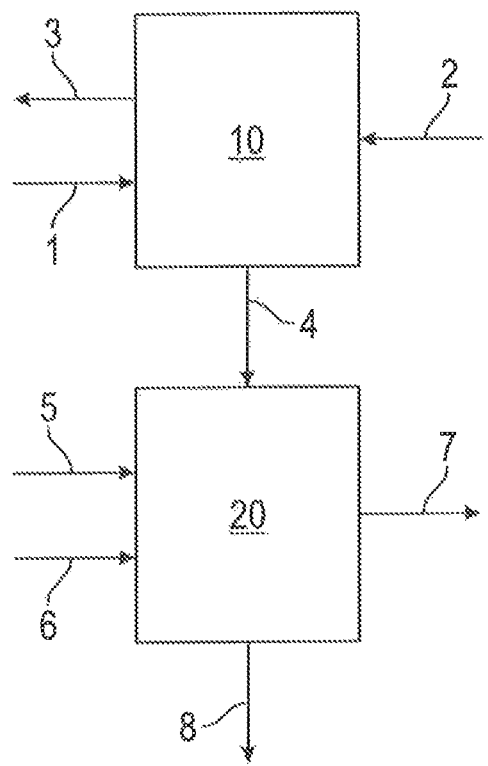
FIG. 1 is a simplified schematic diagram of a generalized version of the MEROX process of the prior art for the liquid-liquid extraction of a combined propane and butane stream.
Figure 2:
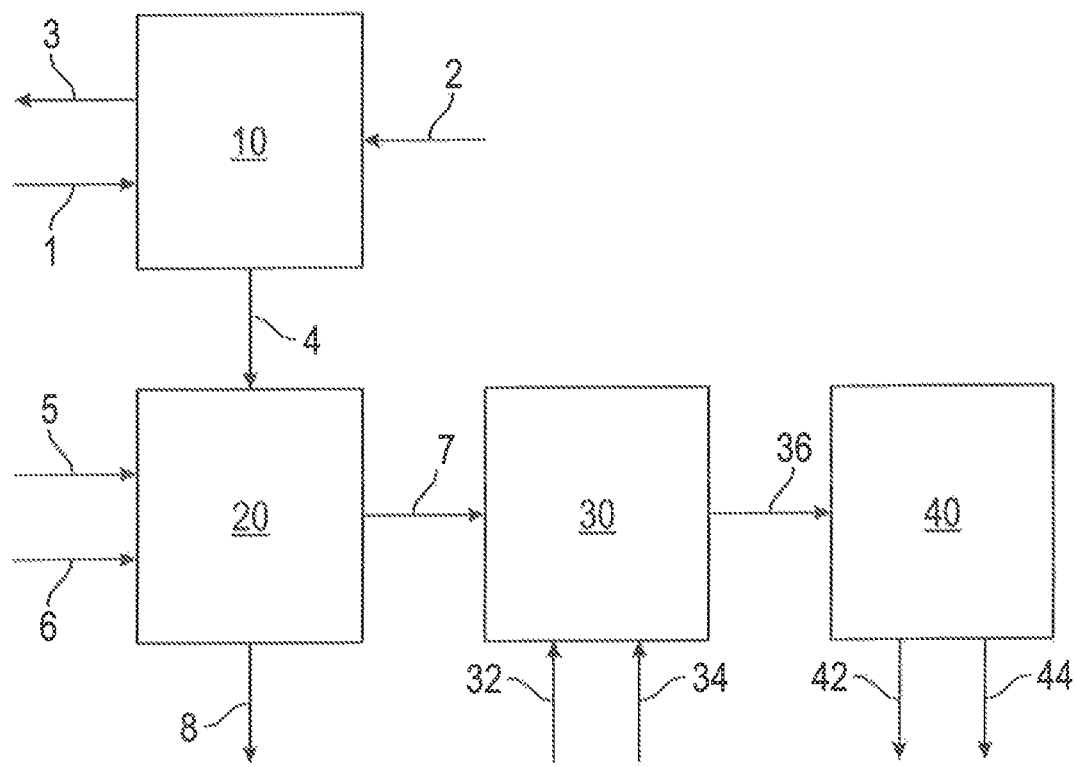
FIG. 2 is a simplified schematic diagram of the integrated process of the present disclosure positioned downstream of the MEROX process of FIG. 1.

An illustrative embodiment of the process and system of the present disclosure will be described with reference to FIG. 2 in which the effluent stream (7) from the generalized MEROX unit of FIG. 1 is treated. It will be understood that the processing of the combined propane and butane stream of FIG. 1 is illustrative only and that separate streams of the products, and combined or separate streams of other mixed and longer chain products can be the subject of the present process for the recovery and oxidation of DSO to produce ODSO compounds.

In order to practice the integrated refinery process of the present disclosure as illustrated in conjunction with the MEROX unit operation of FIG. 1, it is only necessary to add apparatus to recover the by-product DSO compounds from the MEROX process and provide (a) a suitable reactor (30) into which the DSO compounds are introduced in the presence of a catalyst (32) and an oxidant (34) and subjecting the DSO compounds to a catalytic oxidation step to produce the mixed stream (36) of water and oxidized disulfide oil (ODSO) compounds, and (b) a conventional separation vessel (40) to separate the waste water by-product (44) from the ODSO compounds (42). Water soluble ODSO compounds are passed to a fractionation zone (not shown) for recovery following their separation from the waste water fraction. The fractionation zone can include a distillation unit. In certain embodiments, the distillation unit can operate at atmospheric pressure and at a temperature in the range of from 175° C. to 225° C. In other embodiments, the fractionation can be carried out continuously under vacuum conditions. In those embodiments, fractionation occurs at reduced pressures and at their respective boiling temperatures. For example, at 350 mbar and 10 mbar, the temperature ranges are from 147° C. to 194° C. and 75° C. to 98° C., respectively. Following fractionation, the waste water is sent to the waste water pool (not shown) for conventional treatment prior to its disposal. The waste water fraction can contain a small amount of water insoluble ODSO compounds, e.g., in the range of from 1 W % to 1 ppm.

Thus, the capital investment and operating expenses for these two additional units are relatively modest in terms of the values derivable by the refiner from the ODSO products.

Example 1

An oxidation reaction was conducted using disulfide oil compounds that were obtained from a propane and butane MEROX unit. The following were added to a stirred reflux flask: 25.54 g of disulfide oil (R—S—S—R) reactant, 99.15 g of hydrogen peroxide ($H_2O_2$) oxidant, 12.2 g of acetic acid ($CH_3COOH$) phase transfer agent, and 0.23 g of sodium tungstate ($Na_2WO_4.2H_2O$) catalyst which were reacted under reflux at 80° C., with stirring at 400 rpm and the condenser set at 10° C. The reflux was discontinued after 1 hour and, following settling, the clear separation of a water insoluble oil phase and a water soluble oil phase was observed. The water soluble oil phase was rotary evaporated under reduced pressure at 90° C. to recover the product oil. The water insoluble products were subjected to a GC-MS analysis and analyzed for density and sulfur content, and simulated distillation data was prepared. It is noted that the polarity of the more highly oxidized water soluble products precludes GC-MS analysis. Table 2 summarizes the material balance for the reaction of Example 1.

TABLE 2

|  | Amount, g |
|---|---|
| Reactants/Agents | |
| Catalyst | 0.23 |
| Acetic Acid | 12.24 |
| Disulfide Oil | 25.54 |
| Hydrogen Peroxide | 99.15 |
| Total | 137.16 |
| Products | |
| Solids | 0.08 |
| Aqueous | 117.90 |
| Oil | 8.60 |
| Total | 126.59 |
| Mass Balance % | 92.29 |

Product quality improved substantially after the oxidation. Table 3 summarizes the density of the feedstock and the products. Density increases as a function of oxidation. Additionally, the polarity of the products increases as a function of oxidation. Increased oxidation from the water insoluble oxidized DSO (ODSO) products to the water soluble oxidized DSO (ODSO) products results in an increase in polarity and transfer from the oil phase to the water phase.

TABLE 3

| Feedstock/Product | Density, g/cc |
|---|---|
| Disulfide oil | 0.9908 |
| Oxidized disulfide oil (water insoluble) | 1.2573 |
| Oxidized disulfide oil (water soluble) | 1.3818 |

It is noted that the mass balance was low in the examples due to process losses as follows: (a) volatile materials escaping the reflux tube during hydrogen peroxide addition (major); (b) solids remaining on filter paper (minor); (c) residual materials left in glassware (minor); (d) residual materials left in rotary evaporator condenser section (major); and (e) volatile materials escaping rotary evaporator (minor).

Figure 3:
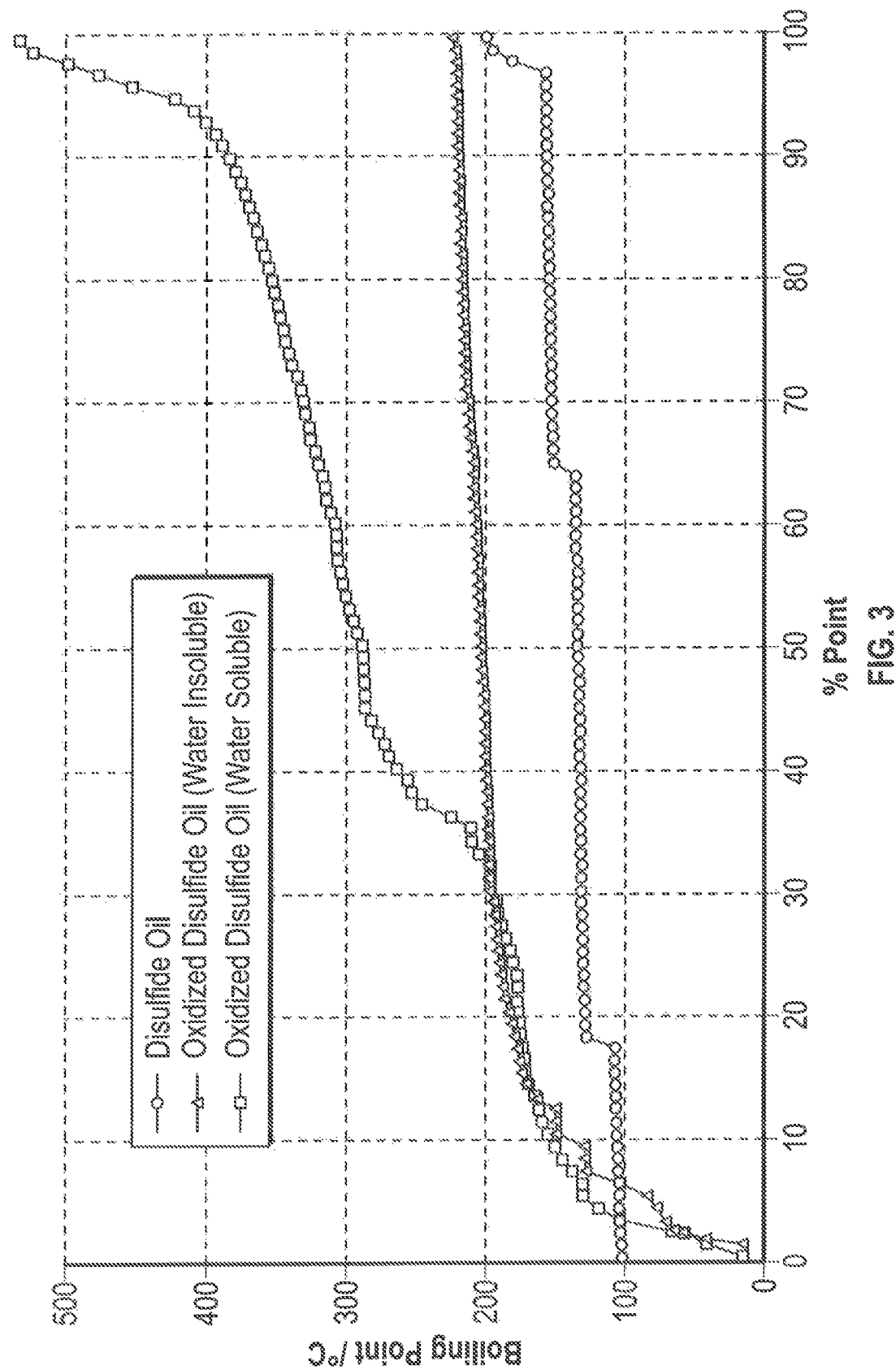
FIG. 3 is a graphic representation of the simulated distillation plots using the ASTM D2887 experimental method showing boiling points in ° C. versus percent for the DSO feed, the water insoluble oil phase and the water soluble oil phase of Example 1.

The data from the simulated distillation of the feedstock and product oil is presented in FIG. 3 and as shown, there is a significant change in boiling point characteristics. The increase in boiling point of the water insoluble ODSO products as compared to the DSO feed reflects the oxidation of the feed. A small portion of the original unreacted feed remains present in the water insoluble ODSO, which is consistent with the GC-MS data. Further oxidizing results in the transfer of the formerly water insoluble ODSO products to the water soluble product layer, which is reflected in the even higher boiling points obtained and a more complex distillation curve reflecting the more complex product distribution. Furthermore, the much higher boiling points of these products significantly lowers the vapor pressure, which helps to reduce the foul and sour smell generally associated with this class of sulfur-containing compounds.

Figure 4:
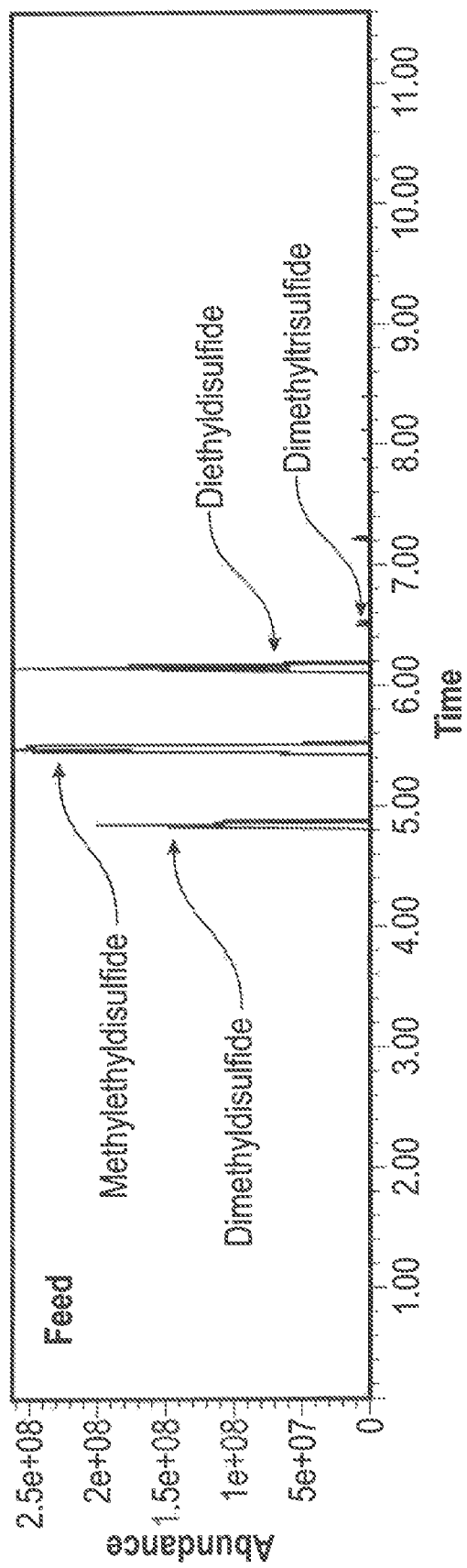
FIG. 4 are reproductions of the gas chromatograms of the disulfide oil feed and the water insoluble phase of Example 1.
Figure 4:
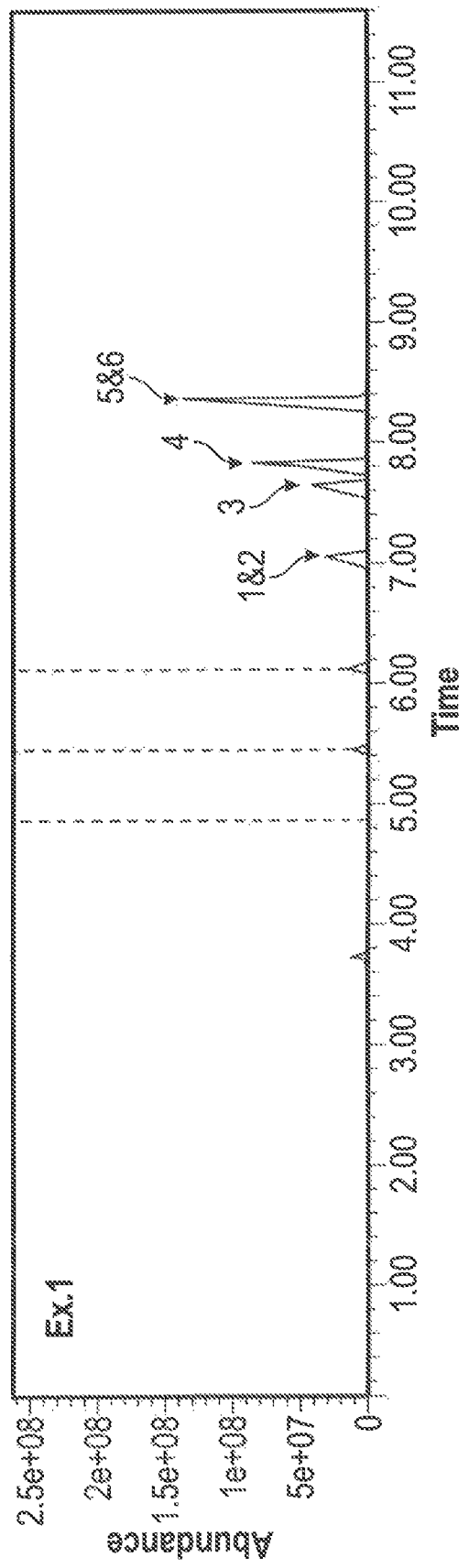

The feedstock and water insoluble ODSO products were analyzed by GC-MS with the results reproduced in FIG. 4. Differences are observed in the chromatographs between the initial disulfide oil feed and the water insoluble oil recovered after the oxidation reaction. The feed sample contains mainly dimethyl disulfide, methyl ethyl disulfide and diethyl disulfide, along with other sulfur species. Based on their area, these three compounds respectively account for about 15.7%, 49.3% and 33.4% of the sample, or 98.4% by weight of the total feed. Among the other species present at trace level, are dimethyl or diethyl trisulfide.

The water insoluble oil product consists principally of the corresponding oxidized derivatives of the disulfide species initially present in the feed, namely, thiosulfonates and disulfoxides. It was noted that for a given symmetrical disulfide compound, i.e., a disulfide compound comprised of two of the same alkyl groups such as dimethyl disulfude or diethyl disulfide, a distinction between the thiosulfonate and the disulfoxide oxidized products was not apparent via GC-MS techniques because of similar product retention times. In contrast, for an asymmetrical disulfide compound, i.e., a disulfide compound comprised of two different alkyl groups such as methylethylsulfide, a distinction between the thiosulfonate and the disulfoxide oxidized products is possible via GC-MS techniques. The $^{13}$C NMR simulation for Example 1 suggests the present of thiosulfonate products.

Table 4 reports the relative weight percentages of the components present in the feedstock and in the products.

TABLE 4

| Concentration, % | Feed | Product | Peak Number |
|---|---|---|---|
| Dimethyldisulfide | 15.7 | 0.2 | |
| Methylethyldisulfide | 49.3 | 1.4 | |
| Diethyldisulfide | 33.4 | 1.5 | |
| Methylmethanethiosulfonate & Dimethyldisulfoxide | — | 10.9 | 1 & 2 |
| Methylethanethiosulfonate | — | 16.3 | 3 |
| Ethylmethyldisulfoxide | — | 24.8 | 4 |
| Ethylethanethiosulfonate & Diethyldisulfoxide | — | 40.6 | 5 & 6 |

The analysis indicates the nearly complete oxidation at 97% of the water insoluble DSO compounds contained in the feed into their respective thiosulfonate and disulfoxide derivatives. In the example, 7% of the product collected was the water insoluble ODSO and 93% of water soluble oxidized DSO (ODSO) was in the aqueous phase.

Example 2

An oxidation reaction was conducted under the same conditions as reported in Example 1, with the exception that compositional changes were made to increase the ratio of the oxidant to the disulfide oil. The composition of the feed is the same as that reported for the feed of Example 1. The following were added to a stirred reflux flask: 20.05 g of disulfide oil (R—S—S—R) reactant, 100.03 g of hydrogen peroxide ($H_2O_2$) oxidant, 9.6 g of acetic acid ($CH_3COOH$) phase transfer agent, and 0.22 g of sodium tungstate ($Na_2WO_4.2H_2O$) catalyst. The reaction proceeded under the same conditions as in Example 1. The two phases were separated after the reflux was discontinued and the water soluble ODSO in the aqueous phase was rotary evaporated under reduced pressure at 90° C. to recover the product oil. The water insoluble products were subjected to GC-MS analysis, and also analyzed for density and sulfur content. Simulated distillation data was prepared. Table 5 summarizes the material balance for Example 2.

TABLE 5

| Reactants/Agents | Amount, g |
|---|---|
| Catalyst | 0.22 |
| Acetic Acid | 9.58 |
| Disulfide Oil | 20.05 |
| Hydrogen Peroxide | 100.03 |
| Total | 129.87 |
| Products | |
| Solids | 0.09 |
| Aqueous | 117.63 |
| Oil | 1.40 |
| Total | 119.10 |
| Mass Balance % | 91.70 |

The mass balance was low due to the same process losses identified in connection with Example 1.

Figure 5:
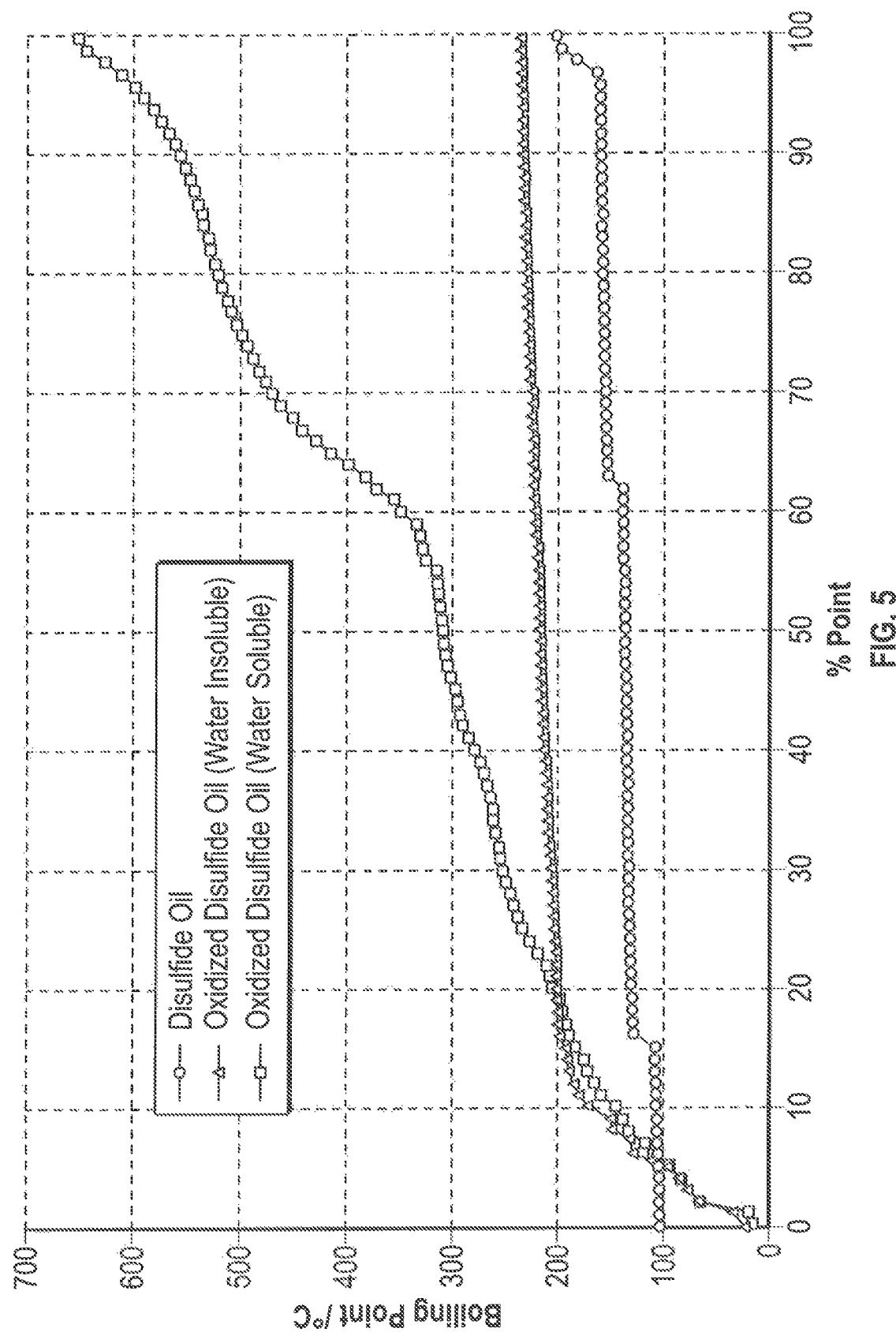
FIG. 5 is a graphic representation of the simulated distillation plots using the ASTM D2887 method showing boiling points in ° C. versus percent for the DSO feed, the water insoluble oil phase and the water soluble oil phase of Example 2.

FIG. 5 illustrates the simulated distillation curves for the feedstock and product oil. As can be seen, there is a significant change in boiling point characteristics.

Figure 6:
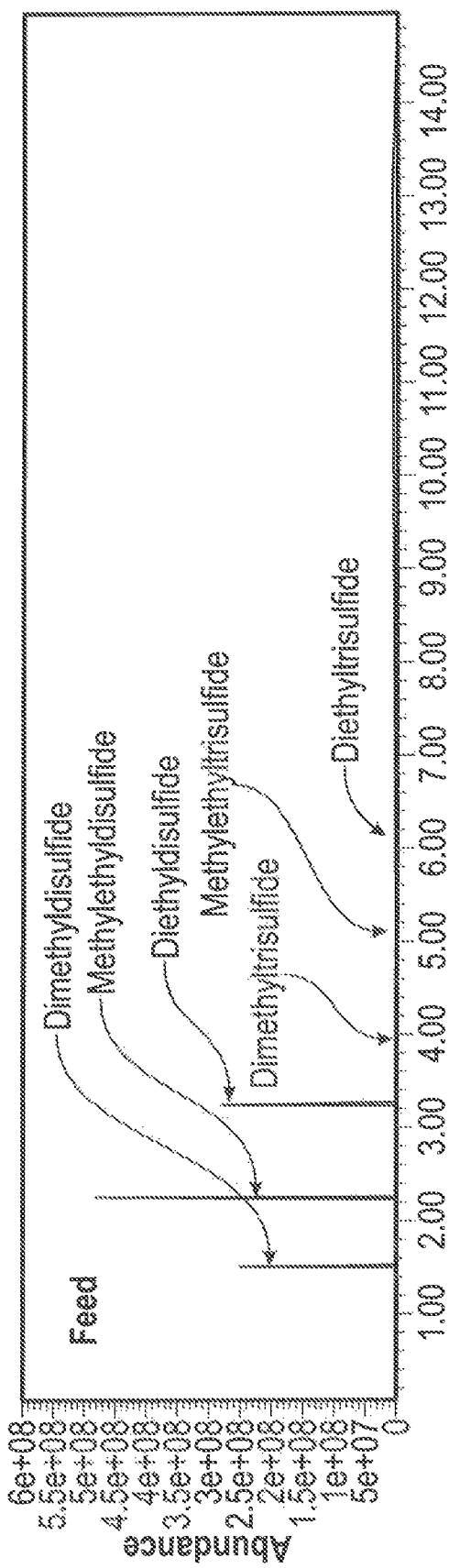
FIG. 6 are reproductions of the gas chromatograms of the disulfide oil feed and the water insoluble phase of Example 2.
Figure 6:
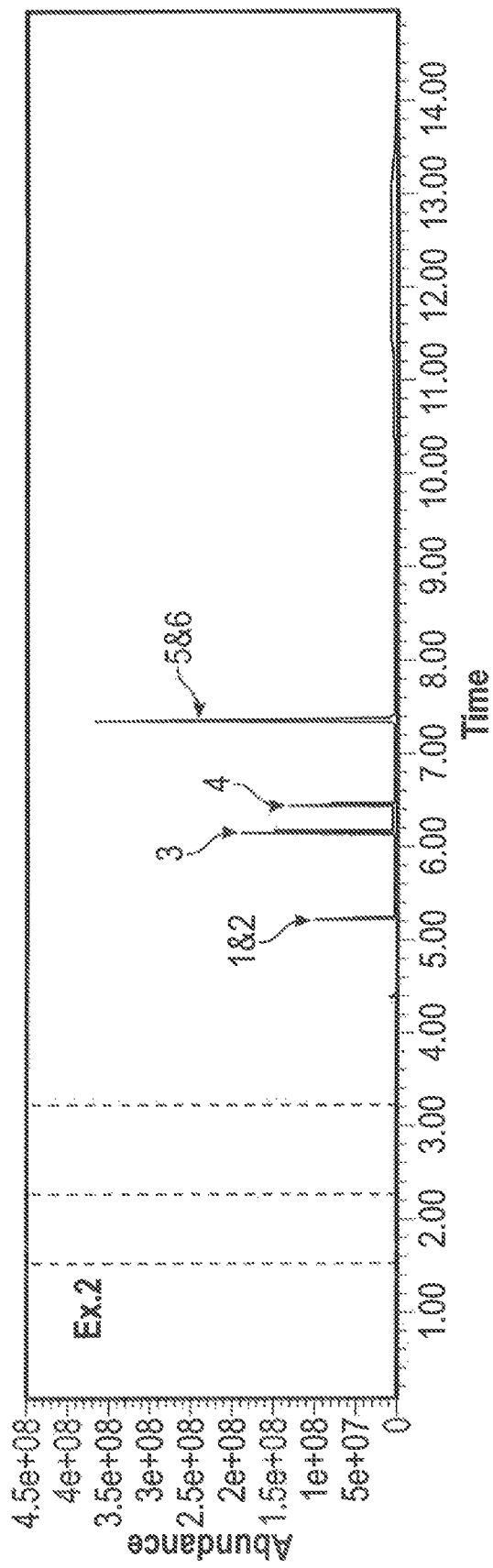

The feedstock and water insoluble products were subjected to GC-MS with the results reproduced in FIG. 6. Differences are observed in the chromatographs between the initial disulfide oil feed and the water insoluble oil recovered after the oxidation reaction of Example 2.

The product consists principally of the oxidized derivatives corresponding to the disulfide species initially present in the feed, namely thiosulfonates and disulfoxides. It was noted that for a given symmetrical disulfide compound, i.e., a disulfide compound comprised of two of the same alkyl groups such as dimethyl disulfude or diethyl disulfide, a distinction between the thiosulfonate and the disulfoxide oxidized products was not apparent via GC-MS techniques because of similar product retention times. In contrast, for an asymmetrical disulfide compound, i.e., a disulfide compound comprised of two different alkyl groups such as methylethyldisulfide, a distinction between the thiosulfonate and the disulfoxide oxidized products is possible via GC-MS techniques.

However, $^{13}C$ NMR simulation for Example 2 suggests the presence of the corresponding thiosulfonate products.

Table 6 reports the relative weight percentages of the components present in the feedstock and in the products.

TABLE 6

| Concentration, % | Feed | Product | Peak Number |
|---|---|---|---|
| Dimethyldisulfide | 15.7 | 0.0 | |
| Methylethyldisulfide | 49.3 | 0.7 | |
| Diethyldisulfide | 33.4 | 0.4 | |
| Methylmethanethiosulfonate & Dimethyldisulfoxide | — | 12.9 | 1 & 2 |
| Methylethanethiosulfonate | — | 22.3 | 3 |
| Ethylmethyldisulfoxide | — | 19.7 | 4 |
| Ethylethanethiosulfonate & Diethyldisulfoxide | — | 40.4 | 5 & 6 |

The analysis indicates the nearly complete oxidation at 99% of the disulfide oil compounds derived from the original feed into their respective water soluble thiosulfonate and disulfoxide derivatives. In the example, 1% of the product collected was the water insoluble ODSO and 99% of water soluble oxidized DSO (ODSO) was in the aqueous phase.

Example 3

An oxidation reaction was conducted under the same conditions as reported in Example 1, with the exception that compositional changes were made to further increase the ratio of the oxidant to the disulfide oil. The following were added to a stirred reflux flask: 17.45 g of disulfide oil (R—S—S—R) reactant, 105.05 g of hydrogen peroxide ($H_2O_2$) oxidant, 8.39 g of acetic acid ($CH_3COOH$) phase transfer agent, and 0.19 g of sodium tungstate ($Na_2WO_4.2H_2O$) catalyst. The reaction proceeded under the same conditions as in Example 1. After the reflux was discontinued, only a water soluble oil phase was found and the product was rotary evaporated under reduced pressure at 90° C. to recover the product oil. Due to its high polarity, the product could not be subjected to GC-MS analysis, but was analyzed for density and sulfur content, and simulated distillation data was prepared. Table 7 summarizes the material balance for Example 3.

TABLE 7

| Reactants/Agents | Amount, g |
|---|---|
| Catalyst | 0.19 |
| Acetic Acid | 8.39 |
| Disulfide Oil | 17.45 |
| Hydrogen Peroxide | 105.05 |
| Total | 131.09 |
| Products | |
| Solids | 0.04 |
| Aqueous | 114.09 |
| Oil | Zero |
| Total | 114.13 |
| Mass Balance % | 87.1 |

Again, the mass balance was low due to the same process losses identified in connection with Example 1.

Table 8 summarizes the density of the feedstock and products. Product quality improved substantially after the oxidation.

TABLE 8

| Feedstock/Product | Density, g/cc |
|---|---|
| Disulfide oil | 0.9908 |
| Oxidized disulfide oil (water insoluble) | Did not form |
| Oxidized disulfide oil (water soluble) | Was not obtained |

Figure 7:
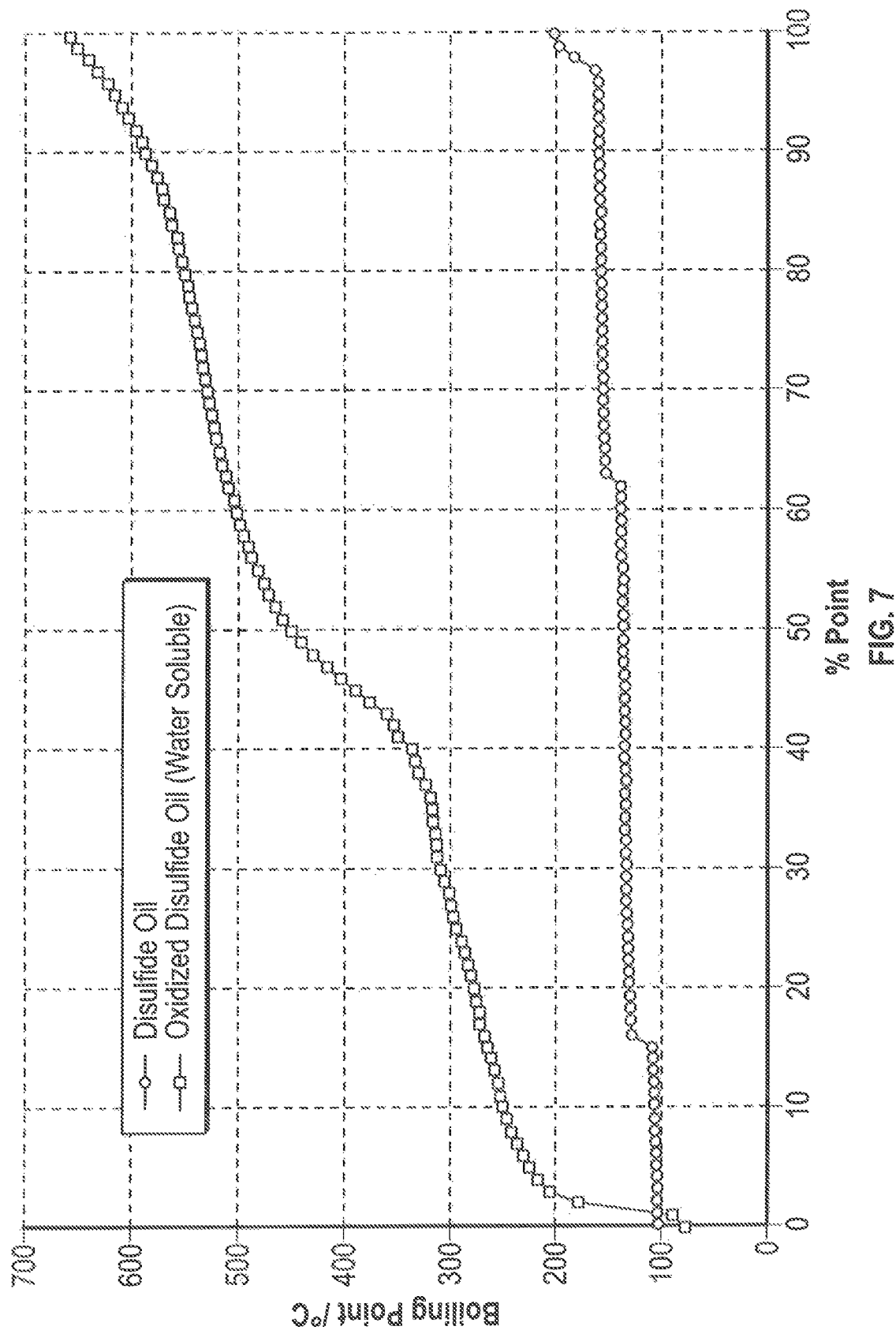
FIG. 7 is a graphic representation of the simulated distillation plots using the ASTM D2887 method showing boiling points in ° C. versus percent for the DSO feed and the water soluble ODSO of Example 3.

FIG. 7 illustrates the simulated distillation curves for the feedstock and product oil. As can be seen, there is a significant change in boiling point characteristics.

At this compositional ratio, only the water soluble oil formed, which as explained above, is "invisible" to GC-MS analysis due to its highly polar character.

Table 9 provides molar ratios of oxidant-to-mono-sulfur. Controlling the degree or extent of oxidation by varying the ratio of oxidant-to-sulfur allows the refiner to control the amount of water soluble oil produced, up to the point where no non-water soluble oil is formed, i.e., only water soluble ODSO is formed. Stated otherwise, this finding permits control of changes in the water soluble oil-to-water insoluble oil ratio.

TABLE 9

|  | Example 1 | Example 2 | Example 3 |
|---|---|---|---|
| Purity of oxidant (wt. %) | 30 | 30 | 30 |
| Mass of oxidant reagent used (g) | 99.15 | 100.02 | 105.05 |
| Moles of oxidant (mol) | 0.87 | 0.88 | 0.93 |
| S content in disulfide oil (wt. %) | 63 | 63 | 63 |
| Av. M.w. of disulfide oil (g/mol) | 109 | 109 | 109 |
| Mass of disulfide oil (g) | 25.54 | 20.05 | 17.45 |
| Moles of mono-S (mol) | 0.469 | 0.368 | 0.320 |
| Molar ratio of oxidant:mono-S | 1.87 | 2.40 | 2.89 |
| Mass fraction of water insoluble oil collected (%) | 6.8 | 1.0 | 0.0 |

As demonstrated by the above examples and the summary of the data presented in Table 9, relatively small changes in the ratio of the oxidant to the starting DSO oils can significantly effect the conversion rate of the reaction that produces water insoluble ODSO. As demonstrated here, the oxidant ratio can be increased to the point that no water insoluble oil is formed.

The ODSO compounds produced by the process described above have utility in related refinery operations such as solvents for aromatic extraction processes, including the selective extraction of targeted aromatic compounds, e.g., benzene from a hydrocarbon feedstream in order to meet specific regulatory requirements. The ODSO compounds can be used alone, or mixed with other known aromatic solvents of the prior art, and can be recovered and recycled for use in the closed system.

The ODSO compounds can also be used as a lubricity additive to significantly increase the lubricity of ultra-low sulfur fuels. The additive is present in low concentrations so that even with its relatively high sulfur content, the finished fuel will meet regulatory requirements. This use can supplement or entirely replace known commercial lubricity additives that must be purchased from third parties. The refiner benefits by utilizing what is typically a waste stream, or at best a low value by-product having limited utility due to environmental concerns, and by avoiding the expense of purchasing lubricity additives from suppliers.

The invention has been described above in detail and illustrated in various embodiments by the examples and the figures, and further embodiments and variations will be apparent to those of ordinary skill in the art from this description so that the scope of protection to be afforded the invention is to be determined by the claims that follows.

The invention claimed is:

1. A process for treating a mercaptan-free hydrocarbon stream comprising disulfide oil compounds derived from a refinery process employed in removing mercaptans from a hydrocarbon stream containing mercaptans, the process comprising:

subjecting the mercaptan-free hydrocarbon stream recovered from the refinery process that comprises the disulfide oil (DSO) compounds to controlled catalytic oxidation in a further refinery process by contacting the disulfide oil compounds in the presence of at least one catalyst with a predetermined molar concentration of at least one oxidant and an organic acid transfer agent to produce an oxidation effluent stream comprising oxidized disulfide oils (ODSO) and waste water;

separating the oxidation effluent stream into a water insoluble oxidized disulfide oil stream and a waste water stream; and recovering the water insoluble oxidized disulfide oil.

2. The process of claim 1 in which the waste water stream comprises a major proportion of water soluble ODSO compounds and a minor proportion of water insoluble ODSO compounds.

3. The process of claim 2 in which the water soluble ODSO compounds in the waste water stream are separated and recovered.

4. The process of claim 1 in which the ODSO compounds contain up to six oxygen atoms.

5. The process of claim 1 in which the molar ratio of the oxidant to sulfur atoms is predetermined to control the proportion of water soluble and water insoluble ODSO compounds produced in the reaction.

6. The process of claim 1 in which the at least one oxidant is a gas phase oxidant selected from the group consisting of air, oxygen, oxides of nitrogen, ozone, and their combinations.

7. The process of claim 1 in which the oxidant is selected from the group consisting of one or more organic hydroperoxides, organic peroxides, and a combination of one or more organic hydroperoxides and organic peroxides.

8. The process of claim 1 in which the oxidant is a liquid phase peroxide selected from the group consisting of alkyl hydroperoxides, aryl hydroperoxides, dialkyl peroxides, diaryl peroxides, peresters and hydrogen peroxide.

9. The process of claim 8 in which the perester has the general formula $R_1C=O—O—O—R_2$, wherein $R_1$ and $R_2$ are the same or different alkyl or aryl groups.

10. The process of claim 1 in which the oxidant is selected from the group of liquid oxidants consisting of one or more organic hydroperoxides, organic peroxides, and a combination of one or more organic hydroperoxides and organic peroxides, and one or more gas phase oxidants selected from the group consisting of one or more of air, oxygen, oxides of nitrogen and ozone.

11. The process of claim 1 in which the DSO oxidation catalyst is a transition metal catalyst.

12. The process of claim 11 in which the transition metal catalyst contains an active species selected from the group consisting of Mo (VI), W (VI), V (V), Ti (IV), and combinations comprising at least one of the foregoing active species.

13. The process of claim 1 in which the oxidation catalyst is sodium tungstate.

14. The process of claim 12 in which the transition metal catalyst exhibits Lewis acid activity.

15. The process of claim 11 in which the oxidation potential of the transition metal catalyst is less than that of the oxidant.

16. The process of claim 1 in which the mercaptan-free hydrocarbon stream comprises a minor proportion of sulfides and a major proportion of disulfide oils.

17. The process of claim 1 in which the molar ratio of the oxidant to sulfur atoms is from 1:1 to 50:1.

18. The process of claim 1 in which the mercaptan-free hydrocarbon stream contains sulfides and disulfides, and the molar ratio of the oxidant to sulfur atoms is from 1:1 to 1:50.

19. The process of claim 1 in which the mercaptan-free hydrocarbon stream contains sulfides and disulfide oils, and the molar ratio of the oxidant to sulfur atoms is from 1.8:1 to 2.9:1.

20. The process of claim 1 in which the molar ratio of the catalyst to the disulfide oil in the oxidation step is from 0.0005 to 0.02.

21. The process of claim 1 in which the catalyst present in the disulfide oil oxidation step is from 0.15 weight % to 5.7 weight % based on the mass flow rate of the sulfides/disulfide oils mixture.

\* \* \* \* \*